US009131863B2

(12) United States Patent
Greenberg et al.

(10) Patent No.: US 9,131,863 B2
(45) Date of Patent: Sep. 15, 2015

(54) INSULATED IMPLANTABLE ELECTRICAL CIRCUIT

(75) Inventors: Robert Greenberg, Los Angeles, CA (US); Neil Hamilton Talbot, Montrose, CA (US); Jerry Ok, Canyon Country, CA (US); Jordan Matthew Neysmith, Pasadena, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 478 days.

(21) Appl. No.: 11/441,993

(22) Filed: May 26, 2006

(65) Prior Publication Data

US 2006/0225274 A1 Oct. 12, 2006

Related U.S. Application Data

(63) Continuation of application No. 10/638,989, filed on Aug. 11, 2003, now Pat. No. 8,380,326.

(60) Provisional application No. 60/402,591, filed on Aug. 9, 2002.

(51) Int. Cl.
*A61N 1/05* (2006.01)
*A61B 5/04* (2006.01)
(Continued)

(52) U.S. Cl.
CPC .......... *A61B 5/04001* (2013.01); *A61N 1/0543* (2013.01); *A61N 1/0551* (2013.01); *A61N 1/0553* (2013.01); *C23C 16/01* (2013.01); *C23C 16/56* (2013.01); *H05K 1/032* (2013.01); *H05K 3/007* (2013.01); *H05K 3/048* (2013.01); *H05K 3/06* (2013.01); *A61B 2562/125* (2013.01); *A61N 1/0529* (2013.01); *H05K 3/28* (2013.01); *H05K 3/4676* (2013.01); *H05K 2201/0179* (2013.01); *H05K 2203/016* (2013.01); *H05K 2203/0502* (2013.01); *H05K 2203/176* (2013.01); *Y10T 29/49124* (2015.01); *Y10T 29/49155* (2015.01)

(58) Field of Classification Search
CPC ......... A61N 1/04; A61N 1/05; A61N 1/0541; A61N 1/0543; H05K 1/032; H05K 2201/0179; H05K 3/007; H05K 3/4676
USPC .......................................... 607/152; 600/372
See application file for complete search history.

(56) References Cited

U.S. PATENT DOCUMENTS 3,699,970 A 10/1972 Brindley et al.
3,977,392 A * 8/1976 Manley .................... 600/392
(Continued)

OTHER PUBLICATIONS

M. Sonn and W. M. Feist, "A Prototype Flexible Microelectrode Array for Implant-Prosthesis Applications," *Medical and Biological Engineering*, 778-791, Nov. 1974.

(Continued)

*Primary Examiner* — Joseph Dietrich
(74) *Attorney, Agent, or Firm* — Scott B. Dunbar

(57) ABSTRACT

The invention is directed to an implantable insulated electrical circuit that utilizes polyparaxylylene, preferably as Parylene, a known polymer that has excellent living tissue implant characteristics, to provide for chronic implantation of conductive electrical devices, such as stimulators and sensors. The device is thin, flexible, electrically insulated, and stable after long exposure to living tissue. Layers of Parylene may be combined with layers of a polymer, such as polyimide, to yield greater design flexibility in the circuit. Multiple electrical conduction layers may be stacked in the circuit to increase packing density.

17 Claims, 1 Drawing Sheet

(51) Int. Cl.
*H05K 1/03* (2006.01)
*H05K 3/00* (2006.01)
*C23C 16/01* (2006.01)
*C23C 16/56* (2006.01)
*H05K 3/04* (2006.01)
*H05K 3/06* (2006.01)
*H05K 3/28* (2006.01)
*H05K 3/46* (2006.01)

(56) References Cited

U.S. PATENT DOCUMENTS

| | | | |
|---|---|---|---|
| 4,573,481 A | | 3/1986 | Bullara et al. |
| 4,837,049 A | | 6/1989 | Byers et al. |
| 5,067,491 A | * | 11/1991 | Taylor et al. ............ 600/561 |
| 5,109,844 A | | 5/1992 | De Juan, Jr. et al. |
| 5,215,088 A | | 6/1993 | Normann et al. |
| 5,476,496 A | * | 12/1995 | Strandberg et al. ........ 607/122 |
| 5,720,099 A | * | 2/1998 | Parker et al. ............. 29/825 |
| 5,935,155 A | | 8/1999 | Humayan et al. |
| 6,374,143 B1 | | 4/2002 | Berrang et al. |
| 6,400,989 B1 | | 6/2002 | Eckmiller |
| 6,458,157 B1 | | 10/2002 | Suaning |
| 7,146,221 B2 | * | 12/2006 | Krulevitch et al. ......... 607/116 |
| 2002/0187260 A1 | * | 12/2002 | Sheppard et al. .......... 427/248.1 |
| 2003/0109903 A1 | * | 6/2003 | Berrang et al. ............ 607/36 |

OTHER PUBLICATIONS

T. Stieglitz, H. Beutel, M. Schuettler, and J.-U. Meyer, "Micromachined, Polyimide-Based Devices for Flexible Neural Interfaces," *Biomedical Microdevices*, 2:4, 283-294, 2000.

B. Ganesh, "A Polyimide Ribbon Cable for Neural Recording and Stimulation Systems," Thesis, University of Utah, Mar. 1998.

A. Schneider, T. Stieglitz, W. Haberer, H. Beutel, and J.-Uwe Meyer, "Flexible Interconnects for Biomedical Microsystems Assembly", IMAPS Conference, Jan. 31, 2001.

* cited by examiner

INSULATED IMPLANTABLE ELECTRICAL CIRCUIT

CROSS-REFERENCES TO RELATED APPLICATIONS

This application is a continuation of application Ser. No. 10/638,989, US Publication No. 20070158100, filed Aug. 11, 2003 now U.S. Pat. No. 8,380,326, which claims the benefit of U.S. provisional Application No. 60/402,591 filed on Aug. 9, 2002, the disclosures of which are hereby incorporated by reference.

FEDERALLY SPONSORED RESEARCH

This invention was made with government support under grant No. R24EY12893-01, awarded by the National Institutes of Health. The government has certain rights in the invention.

FIELD OF THE INVENTION

This invention relates to implantable medical devices, especially implantable cables and electrode arrays for stimulation, recording and interconnection.

BACKGROUND OF THE INVENTION

Arrays of electrodes for neural stimulation are commonly used for a variety of purposes. Some examples include U.S. Pat. No. 3,699,970 to Brindley, which describes an array of cortical electrodes for visual stimulation. Each electrode is attached to a separate inductive coil for signal and power. U.S. Pat. No. 4,573,481 to Bullara describes a helical electrode to be wrapped around an individual nerve fiber. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. U.S. Pat. No. 5,109,844 to de Juan describes a flat electrode array placed against the retina for visual stimulation. U.S. Pat. No. 5,935,155 to Humayun describes a retinal prosthesis for use with a flat retinal array.

Packaging of a biomedical device intended for implantation in the eye, and more specifically for physical contact with the retina, presents a unique interconnection challenge. The consistency of the retina is comparable to that of wet tissue paper and the biological media inside the eye is a corrosive saline liquid environment.

Thus, the device to be placed against the retina, in addition to being comprised of biocompatible, electrochemically stable materials, must appropriately conform to the curvature of the eye, being sufficiently flexible and gentle in contact with the retina to avoid tissue damage, as discussed by Schneider, et al. [see A. Schneider, T. Stieglitz, W. Haberer, H. Beutel, and J.-Uwe Meyer, "Flexible Interconnects for Biomedical Microsystems Assembly," IMAPS Conference, Jan. 31, 2001.] It is also desirable that this device, an electrode array, provides a maximum density of stimulation electrodes. A commonly accepted design for an electrode array is a very thin, flexible circuit cable. It is possible to fabricate a suitable electrode array using discrete wires, but with this approach, a high number of stimulation electrodes cannot be achieved without sacrificing cable flexibility (to a maximum of about 16 electrodes).

Known insulators for implanted electrical circuits include polyimide and silicone dielectrics. They have limited lives once implanted. The polyimide slowly degrades upon exposure to the living tissue and allows water to reach the electrical conductor, eventually leading to at least partial electric current leakage.

Known techniques for implanted electrical circuits do not result in a hermetic package that is suitable for chronic implantation in living tissue. Therefore, it is desired to have an insulated electrical conductor that ensures that the electronic package will function for long-term implant applications in living tissue.

DETAILED DESCRIPTION OF THE PREFERRED EMBODIMENT

Figure 1:
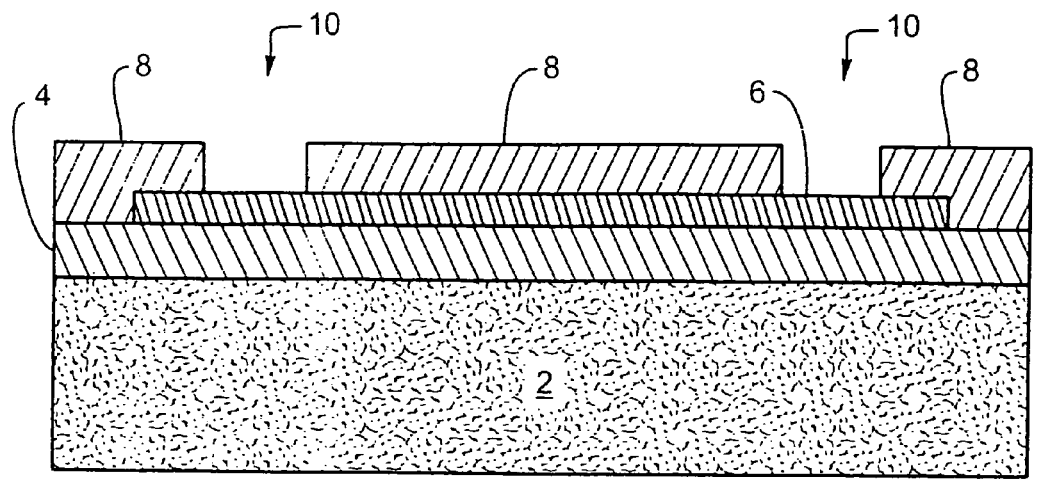
FIG. 1 illustrates a cross-sectional view of an implantable electrical circuit.

The preferred embodiment is an implantable insulated electrical circuit for electrical transmission within living organisms. These assemblies provide electrical conduction, isolation of the electrical conductors from the environment in the living tissue and from each other, and mechanical support for the electrical conductor. Electrical device assemblies that are commonly used for stimulation and or recording within the body benefit from the invention. Neural stimulators or sensors are of particular interest, including retinal electrode arrays. The implantable insulated electrical conductors may also be used to connect discrete components of an implanted medical device, permitting the transmission of electrical signals, power, as well as providing mechanical connection. Key attributes include good electrical insulation properties, low moisture absorption, appropriate mechanical characteristics and ease of fabrication.

Polyparaxylylene is a known polymer that has excellent implant characteristics. One example, Parylene, manufactured by Specialty Coating Systems (SCS), a division of Cookson Electronic Equipment Group, located in Indianapolis, Ind., is a preferred material. Parylene is available in various forms, such as Parylene C, Parylene D, and Parylene N, each having different properties. The preferred form is Parylene C, although it is recognized that many forms of polyparaxylylene may exist or may be developed that are suitable for this application.

The use of Parylene was mentioned, but not pursued, by Sonn and Feist. [see M. Sonn and W. M. Feist, "A Prototype Flexible Microelectrode Array for Implant-Prosthesis Applications," *Medical and Biological Engineering*, 778-791, November 1974.] Stieglitz, et al. published fabrication details of similar items manufactured using polyimide. [see T. Stieglitz, H. Beutel, M. Schuettler, and J.-U. Meyer, "Micromachined, Polyimide-Based Devices for Flexible Neural Interfaces," *Biomedical Microdevices*, 2:4, 283-294, 2000.] Ganesh wrote a thesis on ribbon cables for neural recording and stimulation using polyimide [see B. Ganesh, "A Polyimide Ribbon Cable for Neural Recording and Stimulation Systems," Thesis, University of Utah, March 1998.] Parylene is widely used as an electrical insulating and barrier material in commercial electronic devices. It is well known to use Parylene as a conformal coating on printed circuit boards. While discrete wires have been coated with Parylene for implantation, such as with cochlear implants, the application of Parylene as an electrical insulator for implantable electrical circuits, as embodied by this invention, is unknown to the inventors.

The moisture vapor transmission rates compare favorably with those of other conformal coating materials. The rate for Parylene C is superior to almost all polymeric materials. The Parylenes resist room temperature chemical attack and are insoluble in organic solvents up to 150° C. Parylene C can be dissolved in chloro-napthalene at 175° C., and Parylene N is soluble at the solvent's boiling point (265° C.). The thermal properties are given in Table 1 and the electrical properties are given in Table 2.

substrate 2 may be selected from glass or ceramic, such as alumina or silicon. Substrate 2 is preferably comprised of glass.

A first Parylene layer 4 is deposited on the substrate 2 from a vapor phase that is produced by known techniques, such as thermal decomposition. It is known that Parylene is the polymer "polyparaxylylene" and that any source of this material may be used to implement this invention. The inventors use the term Parylene, as is common in industry practice, to indicate the class of polyparaxylylene polymers.

An electrical conductor 6 is deposited by a known physical vapor deposition method, such as sputtering or evaporation.

TABLE 1

Parylene Thermal Properties(2)

| Properties | Method | Parylene N | Parylene C | Parylene D | Epoxides(1) | Silicones(1) | Urethanes(1) |
|---|---|---|---|---|---|---|---|
| Melting Point (° C.) | 1 | 420 | 290 | 380 | cured | cured | ~170 |
| T5 Point (° C.) (modulus = ($10^5$ psi) | 1 | 160 | 125 | 125 | 110 | ~125 | ~30 |
| T4 Point (° C.) (modulus = ($10^4$ psi) | 1 | >300 | 240 | 240 | 120 | ~80 | 0 |
| Linear Coefficient of Expansion at 25° C. ($\times 10^5$, (° C.)$^{-1}$) | — | 6.9 | 3.5 | 3–8 | 4.5–6.5 | 25–30 | 10–20 |
| Thermal Conductivity at 25° C. ($10^{-4}$ cal/(cm · s · ° C.)) | 2 | 3.0 | 2.0 | — | 4–5 | 3.5–7.5 | 5.0 |
| Specific Heat at 20° C. (cal/g ° C.) | — | 0.20 | 0.17 | — | 0.25 | — | 0.42 |

Test Methods
1. Taken from Secant modulus-temperature curve
2. ASTM C 177
(1)Properties and methods as reported in Modern Plastics Encyclopedia, issue for 1968, Vol. 45/No. 1A, McGraw Hill, New York, 1967
(2)After Specialty Coating Systems, Indianapolis, IN.

While the preferred embodiment is to an electrical conductor

TABLE 2

Parylene Electrical Properties(3)

| Properties(1) | Parylene N | Parylene C | Parylene D | Epoxides(2) | Silicones(2) | Urethanes(2) |
|---|---|---|---|---|---|---|
| Dielectric Strength, dc volts/mil short time, 1 mil films$^a$ | 7,000 | 5,600 | 5.500 | | | |
| Corrected to 1/8 inch | 630 | 500 | 490 | 400–500 | 550 | 450–500 |
| Volume Resistivity ohm-cm, 23° C., 50% RH$^b$ | $1.4 \times 10^{17}$ | $8.8 \times 10^{16}$ | $1.2 \times 10^{17}$ | $10^{12}$–$10^{17}$ | $10^{15}$ | $10^{11}$–$10^{15}$ |
| Surface Resistivity, ohms, 23° C., 50% RH$^b$ | $10^{13}$ | $10^{14}$ | $10^{16}$ | $10^{13}$ | $10^{13}$ | $10^{14}$ |
| Dielectric Constant$^c$ | | | | | | |
| 60 Hz | 2.65 | 3.15 | 2.84 | 3.5–5.0 | 2.7–3.1 | 5.3–7.8 |
| 1 KHz | 2.65 | 3.10 | 2.82 | 3.5–4.5 | 2.6–2.7 | 5.4–7.6 |
| 1 MHz | 2.65 | 2.95 | 2.80 | 3.3–4.0 | 2.6–2.7 | 4.2–5.2 |
| Dissipation Factor | | | | | | |
| 60 Hz | 0.0002 | 0.020 | 0.004 | 0.002–0.01 | 0.001–0.007 | 0.015–0.05 |
| 1 KHz | 0.0002 | 0.019 | 0.003 | 0.002–0.02 | 0.001–0.005 | 0.04–0.06 |
| 1 MHz | 0.0006 | 0.013 | 0.002 | 0.03–0.05 | 0.001–0.002 | 0.05–0.07 |

$^a$ASTM D 149
$^b$ASTM D 257, 1 in$^2$ mercury electrodes
$^c$ASTM D 150, 1 in$^2$
(1)Properties measured on Parylene films, 0.001 in thick.
(2)Properties and methods as reported in Modern Plastics Encyclopedia, issue for 1968, vol. 45, No. 1A, McGraw Hill, NY, 1967.
(3)After Specialty Coating Systems, Indianapolis, IN.

A cross-sectional view of a preferred embodiment of the invention is presented in FIG. 1. An electrical circuit 1 is shown generally being formed on a rigid substrate 2. The 6 that is comprised of one material, it is clear that the electrical conductor 6 may also be comprised of layers of several materials. Alternatively, the conductor 6 or combination thereof may be deposited by other known methods, such as direct write, plating, or electrophoresis. The electrical conductor 6 is patterned by known techniques, such as lift-off or etching. The electrical conductor 6 may be comprised of a single metal or in an alternate embodiment, from several metals that may be layered or alloyed, that are selected from a group of electrically conductive biocompatible materials having favorable electrochemical characteristics, such as titanium, platinum, gold, iridium, and their alloys. Multiple metals may be used in order to achieve desired characteristics. For example, adhesion and barrier layers are commonly used in electronics where individual metal layers are combined to yield a more functional circuit stack. These electrical conduction paths, traces, bond pads, and electrode sites are formed prior to depositing a second layer of Parylene 8 to the device. Typical thicknesses of each Parylene layer are in the range of 0.5 to 50 microns, and preferably are about 3 to 15 microns thick. An alternate embodiment uses metals that are not biocompatible, so long as they are completely encapsulated by the surrounding structural elements and thus do not contact living tissue.

In an alternate embodiment, non-biocompatible materials, such as chrome, silver, or copper may be used as the electrical conductor 6. The electrical conductor 6 is then coated with a biocompatible, hermetic coating in the exposed aperture 6 area. This coating is preferably titanium nitride, although in alternative embodiments it may be an electrically conductive biocompatible metal, such as titanium, platinum, gold, iridium, or their alloys. The Parylene layers cover and protect the rest of the electrical conductor 6.

Apertures 10 are patterned by known techniques, such as by dry etching or laser ablation, or by reactive ion etching. The apertures 10 permit electrical conduction to either tissue or a connected implanted device. The apertures 10 define an electrode area on the electrical conductor 6.

The rigid substrate 2 is removed by known techniques, such as mechanical separation or etching, where mechanical separation is the preferred technique.

As a further embodiment of the invention, adhesion between the first layer of Parylene 4 and the second layer of Parylene 8 is preferably improved by one or more of the following techniques:

(a) Silane application between Parylene layers.
(b) Chemical modification of the Parylene surface to create an energetic, a reactive, or an amorphous surface (Parylene is amorphous as deposited).
(c) Roughening of the Parylene surface.
(d) Thermal compression of the Parylene layers.

Techniques (b) and (c) can used to improve the metal to Parylene adhesion, if applied prior to metal deposition.

More than one electrical conductor 6 may be deposited adjacent to the Parylene. Additional metal layers may be deposited that are protected by additional Parylene layers, such that a multilayered higher density electrical circuit is achieved.

Figure 2:
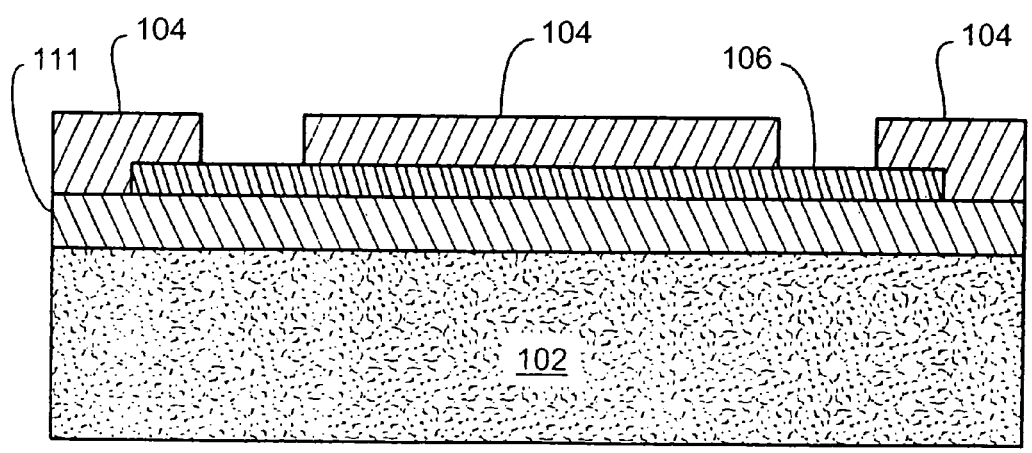
FIG. 2 illustrates a cross-sectional view of an alternate implantable electrical circuit.

A further alternative embodiment, FIG. 2, of the invention preferably replaces the first layer of Parylene 4 with a polymer layer 111, which is preferably polyimide, such that beginning with the rigid substrate 102, the layers are, preferably, polymer layer 111 (polyimide)—electrical conductor 106—layer of Parylene 104. The polyimide is preferably applied as a liquid.

In an alternative embodiment, not illustrated, one applies a first polymer coating, preferably polyimide, prior to depositing the first Parylene layer, such that beginning with the rigid substrate, the layers are, polymer layer (preferably polyimide)—first Parylene layer—electrical conductor—second layer of Parylene.

In yet another embodiment, not illustrated, a polymer coating, preferably of polyimide is applied between the Parylene layer and the electrical conductor.

In further embodiments, not illustrated, a polymer coating, preferably of polyimide is deposited on either side of the second layer of Parylene, either in the presence or absence of a polymer coating on the first layer of Parylene.

Obviously, many modifications and variations of the present invention are possible in light of the above teachings. It is therefore to be understood that, within the scope of the appended claims, the invention may be practiced otherwise than as specifically described.

What is claimed is:

1. A method of manufacturing an insulated flexible electrical circuit suitable for implantation in living tissue comprising:
    providing a substrate;
    depositing by vapor deposition a first polyparaxylylene layer, 0.5 to 50 microns thick on the substrate;
    depositing an electrical conductor layer on the first polyparaxylylene layer;
    patterning the electrical conductor layer to form traces;
    depositing a second polyparaxylylene layer, 0.5 to 50 micros thick, on the first polyparaxylylene layer and on the traces, the second polyparaxylylene layer defining at least one aperture that exposes the traces suitable for electrical communication with living tissue, and
    removing the first polyparaxylylene layer, traces and second polyparaxylylene layer from the substrate;
    wherein the first and second polyparaxylylene layers support the traces.

2. The method according to claim 1, further comprising depositing at least one polymer layer between the first polyparaxylylene layer and the second polyparaxylylene layer.

3. The method according to claim 2, wherein the polymer layer is comprised of polyimide.

4. The method according to claim 1, further comprising depositing at least one polymer layer on the first polyparaxylylene layer or the second polyparaxylylene layer that is not located between the layers.

5. The method according to claim 4, wherein the polymer layer is comprised of polyimide.

6. The method according to claim 1, further comprising depositing a polymer layer between the first polyparaxylylene layer and the electrical traces.

7. The method according to claim 6, wherein the polymer layer is comprised of polyimide.

8. The method according to claim 1, wherein the traces are configured to stimulate a nerve.

9. The method according to claim 1, wherein the traces are configured to sense a signal from a nerve.

10. The method according to claim 1, wherein the second polyparaxylylene layer that defines at least one aperture further defines an electrode site configured to detect or transmit signals to living tissue.

11. The method according to claim 1, wherein the traces are comprised of a biocompatible material.

12. The method according to claim 11, wherein the biocompatible material is selected from the group consisting of titanium, platinum, gold, and iridium.

13. The method according to claim 1, wherein the traces are at least partially coated with a biocompatible material.

14. The method according to claim 13, wherein the biocompatible material is comprised of titanium nitride.

15. The method according to claim 1, further comprising depositing a coating on the traces at the at least one aperture, the coating comprised of biocompatible titanium nitride.

16. The method according to claim 1, further comprising depositing a coating on the traces at the at least one aperture, the coating selected from the biocompatible metal group consisting of titanium, platinum, gold, iridium, and their alloys.

17. The method according to claim 1, further comprising depositing a hermetic coating on the traces at the at least one aperture, the coating selected from the group consisting of titanium nitride, titanium, platinum, gold, iridium, and their alloys.

* * * * *